(12) United States Patent
Ueda et al.

(10) Patent No.: US 8,063,254 B2
(45) Date of Patent: Nov. 22, 2011

(54) METHOD FOR PRODUCTION OF REDUCED COENZYME $Q_{10}$ USING WATER-CONTAINING ORGANIC SOLVENT

(75) Inventors: Takahiro Ueda, Osaka (JP); Shiro Kitamura, Takasago (JP)

(73) Assignee: Kaneka Corporation, Osaka-shi (JP)

( * ) Notice: Subject to any disclaimer, the term of this patent is extended or adjusted under 35 U.S.C. 154(b) by 0 days.

(21) Appl. No.: 12/740,086

(22) PCT Filed: Oct. 29, 2008

(86) PCT No.: PCT/JP2008/069590
§ 371 (c)(1),
(2), (4) Date: Apr. 27, 2010

(87) PCT Pub. No.: WO2009/057611
PCT Pub. Date: May 7, 2009

(65) Prior Publication Data
US 2010/0234643 A1    Sep. 16, 2010

(30) Foreign Application Priority Data
Oct. 30, 2007    (JP) ................. 2007-282215

(51) Int. Cl.
*C07C 35/18*    (2006.01)
*C07C 35/12*    (2006.01)
(52) U.S. Cl. ...................... 568/823; 868/830
(58) Field of Classification Search ............... 568/823, 568/830
See application file for complete search history.

(56) References Cited

U.S. PATENT DOCUMENTS
6,184,255 B1    2/2001    Mae et al.
2004/0214301 A1    10/2004    Ueda et al.
2004/0215040 A1    10/2004    Ueda et al.
2004/0236154 A1    11/2004    Ueda et al.
2005/0008630 A1    1/2005    Ueda et al.
2006/0246565 A1    11/2006    Ueda et al.

FOREIGN PATENT DOCUMENTS
| JP | 10-109933 A | 4/1998 |
| JP | 2003-089669 A | 3/2003 |
| JP | 2006-513274 A | 4/2006 |
| WO | WO 03/006408 A1 | 1/2003 |
| WO | WO 03/006409 A1 | 1/2003 |
| WO | WO 03/006412 A1 | 1/2003 |
| WO | WO 03/032967 A1 | 4/2003 |

OTHER PUBLICATIONS

Foti et al., *Journal of American Chemical Society*, 116(21): 9440-9447 (1994).

*Primary Examiner* — Sikarl Witherspoon
(74) *Attorney, Agent, or Firm* — Leydig, Voit & Mayer, Ltd.

(57) ABSTRACT

The present invention aims to provide reduced coenzyme Q10, which is useful as food, food with nutrient function claims, food for specified health use, nutritional supplement, nutritional product, animal drug, drink, feed, cosmetic, pharmaceutical product, therapeutic drug, prophylactic drug and the like, and a production method of reduced coenzyme $Q_{10}$. The present invention provides a production method of reduced coenzyme $Q_{10}$, which includes reducing oxidized coenzyme $Q_{10}$ with ascorbic acid or its analogue(s) as a reducing agent in a water-containing organic solvent at not more than pH 5. Using the method, the reaction time can be drastically shortened even without adding a basic substance and the like, and unpreferable side reactions can be minimized. Therefore, reduced coenzyme $Q_{10}$ with high quality can be produced.

13 Claims, No Drawings

METHOD FOR PRODUCTION OF REDUCED COENZYME $Q_{10}$ USING WATER-CONTAINING ORGANIC SOLVENT

TECHNICAL FIELD

The present invention relates to a production method of reduced coenzyme $Q_{10}$. As compared to oxidized coenzyme $Q_{10}$, reduced coenzyme $Q_{10}$ shows high oral absorbability, and is a compound useful as a superior food, food with nutrient function claims, food for specified health use, nutritional supplement, nutritional product, animal drug, drink, feed, cosmetic, pharmaceutical product, therapeutic drug, prophylactic drug, pet food and the like.

BACKGROUND ART

Oxidized coenzyme $Q_{10}$, which is a benzoquinone derivative widely distributed in the living world, is also called vitamin Q due to its function like a vitamin, and is a component that rejuvenates the body as a nutrient source that brings weak cell activity to a healthy state. On the other hand, reduced coenzyme $Q_{10}$ is a two-electron reduction form of oxidized coenzyme $Q_{10}$, and oxidized coenzyme $Q_{10}$ is an orange crystal, whereas reduced coenzyme $Q_{10}$ is a white crystal. Reduced coenzyme $Q_{10}$ and oxidized coenzyme $Q_{10}$ are localized in mitochondria, lysosome, golgi apparatus, microsome, peroxisome, cellular membrane and the like, and are indispensable substances for the maintenance of biological functions, which are known to be involved in the activation of ATP production, antioxidant action in the body and stabilization of membrane as a constituent component of the electron transport system.

As a production method of reduced coenzyme $Q_{10}$, it is known to be obtained, for example, by a method comprising producing coenzyme $Q_{10}$ by a conventionally known method such as synthesis, fermentation, extraction from a naturally occurring substance and the like, and concentrating a reduced coenzyme $Q_{10}$ fraction in an eluate from chromatography and the like (patent reference 1: JP-A-H10-109933). The patent reference 1 describes that, in this case, oxidized coenzyme $Q_{10}$ contained in the above-mentioned reduced coenzyme $Q_{10}$ may be reduced with a reducing agent such as sodium borohydride, sodium hydrosulfite (sodium dithionite) and the like, and concentrated by chromatography, and that the reduced coenzyme $Q_{10}$ can also be obtained by a method comprising reacting existing highly pure coenzyme $Q_{10}$ with the above-mentioned reducing agent.

In addition, a method of reducing oxidized coenzyme $Q_{10}$ to reduced coenzyme $Q_{10}$ by using ascorbic acid or its analogue(s) is also known (non-patent document 1: J. Am. Chem. Soc., 1990, 116, 9440-9447). In this document, a reduction reaction of oxidized coenzyme $Q_{10}$ is performed in a mixed solvent of ethanol/water in the presence of sodium hydroxide.

On the other hand, the present inventors have also filed some patent applications relating to reduction reaction of oxidized coenzyme $Q_{10}$ by using ascorbic acid or its analogue(s) as reducing agent (e.g., patent documents 2-4: WO03/006408, WO03/006409, WO03/032967). These patent documents describe that oxidized coenzyme $Q_{10}$ can be reduced by using ascorbic acids or its analogue(s), a water-soluble organic solvent or water can be used as solvents, and a basic substance and bisulfite are added as reaction promoters.

However, oxidized coenzyme $Q_{10}$, which is the starting material of these reduction reactions, and reduced coenzyme $Q_{10}$, which is the resultant product, do not dissolve in water. Therefore, when water is used during reduction reaction, 2-phase reactions are generally employed requiring a large amount of water, which is not entirely advantageous from the aspects of volume efficiency and the like. As mentioned above, addition of a reaction promoter such as a basic substance, bisulfite and the like is generally proposed to shorten the reaction time of reduction reactions by using ascorbic acids or its analogue(s). When such a reaction promoter is used, incorporation of a separate step of removing the above-mentioned reaction promoter before obtaining reduced coenzyme $Q_{10}$ also needs to be considered.

patent document 1: JP-A-10-109933
patent document 2: WO03/006408
patent document 3: WO03/006409
patent document 4: WO03/032967
non-patent document 1: J. Am. Chem. Soc., 1990, 116, 9440-9447

DISCLOSURE OF THE INVENTION

Problems to be Solved by the Invention

As mentioned above, a report has documented that the reaction time can be shortened by performing a general reduction reaction using ascorbic acids or its analogue(s) as a reducing agent in the presence of a basic substance. The present inventors have preliminarily studied the method in the reduction reaction of oxidized coenzyme $Q_{10}$, and clarified that, under the conditions described in the above-mentioned non-patent document 1, for example, a reduction reaction of oxidized coenzyme $Q_{10}$ proceeds halfway but does not proceed completely, and highly pure reduced coenzyme $Q_{10}$ cannot be obtained.

In view of the above, the present invention aims to shorten the reaction time without using other additive in addition to ascorbic acid and its analogue(s), and obtain highly pure reduced coenzyme $Q_{10}$.

Means of Solving the Problems

The present inventors have studied and found that the reaction time can be drastically shortened and highly pure reduced coenzyme $Q_{10}$ can be produced even without using the aforementioned reaction promoter, by using a water-containing organic solvent containing a small amount of water as a reaction solvent and setting the pH of the reaction solution to not more than 5.

That is, the present invention relates to, in a method of producing reduced coenzyme $Q_{10}$ by reducing oxidized coenzyme $Q_{10}$ with ascorbic acid or its analogue(s), a production method of reduced coenzyme $Q_{10}$ comprising performing a reduction reaction using a water-containing organic solvent as a reaction solvent and under the conditions of pH 5 or below.

Moreover, the present invention preferably relates to (1) the above-mentioned production method of obtaining a reduced coenzyme $Q_{10}$ crystal, comprising crystallizing reduced coenzyme $Q_{10}$ from a reaction mixture after the reduction reaction, and performing a solid-liquid separation, (2) the above-mentioned production method comprising adding, after the reduction reaction, an organic solvent and/or water to the reaction mixture, separating an organic layer containing reduced coenzyme $Q_{10}$ from an aqueous layer to give the organic layer, crystallizing the reduced coenzyme $Q_{10}$ from the organic layer, and performing a solid-liquid separation to give the reduced coenzyme $Q_{10}$ crystal, and (3) the above-mentioned production method comprising adding, after the reduction reaction, an organic solvent and/or water to the reaction mixture, separating an organic layer containing reduced coenzyme $Q_{10}$ from an aqueous layer to give the organic layer, and evaporating the solvent from the organic layer to give reduced coenzyme $Q_{10}$ as an oily substance or a solid.

Effect of the Invention

According to the present invention, lowering of volume efficiency in the reduction reaction can be minimized, and the reduction reaction time can be shortened even without using a reaction promoter that requires removal in a later step, and therefore, highly pure reduced coenzyme $Q_{10}$ can be obtained conveniently.

BEST MODE FOR CARRYING OUT THE INVENTION

The present invention is explained in detail in the following. In the present specification, an indication of coenzyme $Q_{10}$ alone does not question whether it is oxidized type or reduced type. When the two are mixed, the term refers to the mixture as a whole.

The production method of the present invention is characterized in that ascorbic acid or its analogue(s) is used as a reducing agent and a water-containing organic solvent is used as a reaction solvent, a reduction reaction of oxidized coenzyme $Q_{10}$ is performed under the conditions of pH of not more than 5 to give reduced coenzyme $Q_{10}$.

The oxidized coenzyme $Q_{10}$ to be used as the starting material in the production method of the present invention may be prepared by synthesis, fermentation, extraction from a naturally occurring substance, and the like, and may be existing highly pure coenzyme $Q_{10}$, which is generally commercially available. In addition, it may contain only oxidized coenzyme $Q_{10}$, or may be a mixture of oxidized coenzyme $Q_{10}$ and reduced coenzyme $Q_{10}$.

The production method of the present invention requires use of a water-containing organic solvent as a reaction solvent for a reduction reaction. The water-containing organic solvent in this case is not particularly limited as long as it is an organic solvent containing water, i.e., a mixed solvent of water and an organic solvent. Preferably, water and an organic solvent are in a compatible state, that is, they are homogeneously mixed. From such aspects, the organic solvent in the water-containing organic solvent to be used as a reaction solvent in the above-mentioned reduction reaction is preferably a water-soluble organic solvent dissolved in water at an optional or particular mixing ratio. Such organic solvent is not particularly limited and, for example, alcohols, ketones, nitriles, ethers and the like can be mentioned.

The above-mentioned alcohols may be cyclic or acyclic, saturated or unsaturated and are not particularly limited. Generally, saturated ones are preferably used. For example, monovalent alcohol having 1 to 5 carbon atoms, particularly 1 to 4 carbon atoms, especially 1 to 3 carbon atoms, most of all 2 or 3 carbon atoms, divalent alcohol having 2 to 5 carbon atoms, or trivalent alcohol having 3 carbon atoms is preferable.

Examples of the monovalent alcohol include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol and the like. Preferred are methanol, ethanol, 1-propanol, 2-propanol, 1-butanol, 2-butanol, isobutyl alcohol and tert-butyl alcohol, more preferred are methanol, ethanol, 1-propanol and 2-propanol, further preferred are ethanol, 1-propanol or 2-propanol, most preferred is ethanol.

Examples of the divalent alcohol include 1,2-ethanediol, 1,2-propanediol, 1,3-propanediol, 1,2-butanediol, 1,3-butanediol, 1,4-butanediol, 2,3-butanediol, 1,5-pentanediol and the like. Preferred are 1,2-ethanediol, 1,2-propanediol and 1,3-propanediol, most preferred is 1,2-ethanediol.

As the trivalent alcohol, glycerol and the like can be preferably used.

The above-mentioned ketones are not particularly limited, and those generally having 3 to 6 carbon atoms are preferably used. Specific examples include acetone, methyl ethyl ketone, methyl butyl ketone, methyl isobutyl ketone and the like. Preferred are acetone and methyl ethyl ketone, and most preferred is acetone.

The above-mentioned nitriles may be cyclic or acyclic, saturated or unsaturated and are not particularly limited. Generally saturated ones are preferably used. Normally, those having 2 to 8 carbon atoms, particularly 2 to 6 carbon atoms, especially 2 to 4 carbon atoms, are preferably used.

Specific examples include acetonitrile, propionitrile, malononitrile, butyronitrile, isobutyronitrile, succinonitrile, valeronitrile, glutaronitrile, hexanenitrile, heptyl cyanide, chloroacetonitrile, bromoacetonitrile, chloropropionitrile, bromopropionitrile, methoxyacetonitrile, methyl cyanoacetate, ethyl cyanoacetate, chlorobenzonitrile, bromobenzonitrile and the like.

Preferred are acetonitrile, propionitrile, succinonitrile, butyronitrile, isobutyronitrile, valeronitrile, methyl cyanoacetate and ethyl cyanoacetate, more preferred are acetonitrile, propionitrile, butyronitrile and isobutyronitrile, most preferred is acetonitrile.

The above-mentioned ethers may be cyclic or acyclic, saturated or unsaturated and are not particularly limited. Generally, saturated ones are preferably used. Normally, those having 3 to 12 carbon atoms, particularly 4 to 8 carbon atoms, especially 4 to 8 carbon atoms, are preferably used.

Specific examples include diethyl ether, methyl tert-butyl ether, dipropyl ether, diisopropyl ether, dibutyl ether, dihexyl ether, ethylvinyl ether, butylvinyl ether, anisole, phenetol, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol dibutyl ether and the like.

Preferred are diethyl ether, methyl tert-butyl ether, dipropyl ether, diisopropyl ether, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether and ethylene glycol monoethyl ether, more preferred are diethyl ether, methyl tert-butyl ether, dioxane, tetrahydrofuran, ethylene glycol monomethyl ether and ethylene glycol monoethyl ether, still more preferred are diethyl ether, methyl tert-butyl ether, dioxane, tetrahydrofuran and the like, and most preferred are dioxane and tetrahydrofuran.

Needless to say, a plurality of the above-mentioned organic solvents may be used in combination.

The organic solvent is preferably selected from among the above-mentioned organic solvents in consideration of properties such as boiling point, viscosity and the like. Specifically, for example, the organic solvent has a boiling point of about 30° C.-150° C. under 1 atm since suitable heating to increase the solubility and reaction rate can be allowed and the solvent including wet masses can be easily removed by drying or the solvent of a crystallization filtrate can be easily recovered etc., the organic solvent has, for example, a melting point of not more than about 20° C., preferably not more than about 10° C., more preferably about 0° C. or below since it is not easily solidified during handling at room temperature and when cooled to room temperature or below and, for example, the organic solvent has a low viscosity of about 10 cp or below at 20° C., and the like. Particularly, from the aspects of industrial operation, an organic solvent that is not easily volatilized at ambient temperature is preferable, and generally, for example, an organic solvent having a boiling point of not less than about 50° C., further not less than about 55° C., is preferable.

In consideration of the above-mentioned properties, cost, recyclability, easiness of availability, and use for food and pharmaceutical products, the organic solvent to be used for the reduction reaction is preferably methanol, ethanol, 1-propanol, 2-propanol or acetone, more preferably methanol, ethanol or 2-propanol, most preferably ethanol.

In the production method of the present invention, the content of water in a water-containing organic solvent, which is a reaction solvent for the reduction reaction, namely, the weight ratio of an organic solvent and water in the water-containing organic solvent, exerts a great influence on the reaction time. The weight ratio of an organic solvent and water in the water-containing organic solvent cannot be defined generally since it is affected by the kind of the organic solvent to be used. When the weight ratio of water in the organic solvent is small, the effect of shortening of the reaction time is also small. On the other hand, when the weight ratio of water is too high, the weight ratio of an organic solvent becomes relatively low. As a result, for example, a layer containing oxidized coenzyme $Q_{10}$ and/or reduced coenzyme $Q_{10}$ and a layer containing water tend to be separated, and it leads to an extended reaction time. To suppress separation of these two layers, the amount of the water-containing organic solvent itself to be used may be increased. However, it is not preferable from the aspects of volume efficiency during reaction and the like.

From such aspects, the upper limit of the water content in the water-containing organic solvent is preferably about 15 wt %, more preferably about 13 wt %, further preferably about 10 wt %, and the lower limit is preferably about 1 wt %, more preferably about 3 wt %, further preferably about 5 wt %. In other words, the weight ratio of the organic solvent and water in the water-containing organic solvent is preferably within the range of about 99/1-85/15, more preferably about 97/3-87/13, further preferably about 95/5-90/10. A method of preparing the water-containing organic solvent at such ratio is not particularly limited, and water in the water-containing organic solvent may or may not be added from the outside.

In the production method of the present invention, the ascorbic acid and its analogues to be used as a reducing agent are not particularly limited and, for example, not only ascorbic acid but also those analogous to ascorbic acid such as rhamno-ascorbic acid, arabo-ascorbic acid, gluco-ascorbic acid, fuco-ascorbic acid, glucohepto-ascorbic acid, xylo-ascorbic acid, galacto-ascorbic acid, gulo-ascorbic acid, allo-ascorbic acid, erythro-ascorbic acid, 6-desoxyascorbic acid and the like are contained. In addition, an ester or salt thereof can also be used.

They may also be an L form, a D form or a racemate. Specific examples include L-ascorbic acid, L-ascorbyl palmitate, L-ascorbyl stearate, D-arabo-ascorbic acid and the like. In the production method of the present invention, any of the above-mentioned ascorbic acid and its analogues can be preferably used as the reducing agent. In consideration of easy separation from the resulting reduced coenzyme $Q_{10}$ and the like, particularly water-soluble ones are used from among the above-mentioned ascorbic acid and its analogues. Specifically, from among the above-mentioned ascorbic acid and its analogues, a free form or a salt is preferably used. Most preferably, a free form of L-ascorbic acid, D-arabo-ascorbic acid and the like is used from the aspects of easy availability, cost and the like.

The amount of the above-mentioned ascorbic acid and its analogues to be used is not particularly limited, and only needs to be an effective amount that can convert all (or most) of oxidized coenzyme $Q_{10}$, which is a starting material, to reduced coenzyme $Q_{10}$. Generally, an effective amount of ascorbic acid and its analogues that can convert all of oxidized coenzyme $Q_{10}$ to reduced coenzyme $Q_{10}$ is generally not less than one or more moles per mole, preferably not less than 1.2 or more moles per mole, relative to oxidized coenzyme $Q_{10}$. While the upper limit is not particularly limited, in consideration of the economic aspect, it is normally 10 or more moles per mole, preferably 5 or more moles per mole, more preferably 3 or more moles per mole.

In the production method of the present invention, the reduction reaction of oxidized coenzyme $Q_{10}$ is performed under conditions of not more than pH 5, preferably not more than pH 4, still more preferably pH 2 to 4. The pH value here is that of the entire reaction mixture in the reduction reaction. In the present invention, at least pH at the time of the start of the reaction needs to fall within the above-mentioned range, and the pH value preferably falls within the above-mentioned range throughout the reduction reaction. A method of controlling the above-mentioned pH value in the present invention is not particularly limited, and an acid or base may be used to control the pH value, or any special pH control means may not be required.

While the acid usable for the pH control is not particularly limited, inorganic acids such as sulfuric acid, hydrogen chloride (including hydrochloric acid), phosphoric acid and the like; organic acids such as sulfonic acid (e.g., methanesulfonic acid, ethanesulfonic acid, benzenesulfonic acid, p-toluenesulfonic acid and the like), carboxylic acid (e.g., trifluoroacetic acid, trichloroacetic acid and the like), citric acid, malic acid etc., and the like can be used. Among these, inorganic acids such as sulfuric acid, hydrogen chloride, phosphoric acid and the like are preferable.

The base usable for the pH control is not particularly limited and, for example, alkali metal carbonates such as sodium carbonate and the like, alkali metal hydrogencarbonates such as sodium hydrogen carbonate and the like, alkaline earth metal carbonates such as magnesium carbonate and the like, amines such as ammonia, triethylamine etc. and the like can be used. Among these, weak bases such as metal (preferably alkali metal, alkaline earth metal etc.) carbonate, hydrogencarbonate, ammonia, amine and the like are preferable from the aspect of easy pH control.

In the production method of the present invention, the reduction reaction is preferably performed under a forced flow. Specifically, the mechanical power necessary for stirring per unit volume is generally not less than about 0.01 kW/m³, preferably not less than about 0.1 kW/m³, more preferably not less than about 0.3 kW/m³ is preferable. The above-mentioned forced flow is generally produced by rotation of impeller. However, as long as the above-mentioned flow is obtained, an impeller does not always need to be used and, for example, a method by a liquid circulation and the like may be utilized.

In the production method of the present invention, the reduction reaction is generally performed at not less than 30° C., preferably not less than 40° C., more preferably not less than 50° C. The upper limit of the reduction reaction temperature is not more than the boiling point of the system. The reduction reaction can be preferably performed generally at about 30-150° C., preferably about 40-120° C., more preferably about 50-100° C.

In the production method of the present invention, the initial concentration of oxidized coenzyme $Q_{10}$ relative to the reaction solvent for performing the reduction reaction is not particularly limited. In general, the weight of oxidized coenzyme $Q_{10}$ per 100 parts by weight of a water-containing organic solvent is normally not less than about 1 part by weight, preferably not less than 3 parts by weight, more preferably not less than 5 parts by weight, especially not less than 10 parts by weight. While the upper limit is not particularly limited, it is normally not more than about 60 parts by weight, preferably not more than 50 parts by weight, more preferably not more than 40 parts by weight, especially not more than 30 parts by weight. In general, the method can be preferably performed when the weight of oxidized coenzyme $Q_{10}$ per 100 parts by weight of a water-containing organic solvent is about 1-30 parts by weight, preferably about 5-30 parts by weight, more preferably about 10-30 parts by weight.

In the production method of the present invention, the reduction reaction varies depending on the kind and amount of the ascorbic acid and its analogues to be used, and cannot be defined generally. Generally, the method can be completed in 24 hr, preferably 20 hr, more preferably 15 hr, especially 10 hr. The weight ratio of reduced coenzyme $Q_{10}$/oxidized coenzyme $Q_{10}$ after completion of the reduction reaction can be expected to be not less than 97/3, preferably not less than 98/2, more preferably not less than 99/1.

In the production method of the present invention, reduced coenzyme $Q_{10}$ is preferably isolated from the reaction mixture sequentially after the above-mentioned reduction reaction. While the method of isolating reduced coenzyme $Q_{10}$ from the reaction mixture is not particularly limited, for example, the following method can be mentioned.

method 1: a method of obtaining a reduced coenzyme $Q_{10}$ crystal, comprising directly crystallizing reduced coenzyme $Q_{10}$ from a reaction mixture after the reduction reaction, and performing a solid-liquid separation, method 2: a method of obtaining a reduced coenzyme $Q_{10}$ crystal, comprising adding an organic solvent and/or water to the reaction mixture to transfer reduced coenzyme $Q_{10}$ to an organic layer, separating the organic layer containing reduced coenzyme $Q_{10}$ from an aqueous layer to give the organic layer, where necessary, washing the organic layer with water and substituting the solvent, crystallizing the reduced coenzyme $Q_{10}$ from the organic layer, and performing a solid-liquid separation to give the reduced coenzyme $Q_{10}$ crystal, and method 3: a method of obtaining a reduced coenzyme $Q_{10}$ crystal, comprising adding an organic solvent and/or water to the reaction mixture to transfer reduced coenzyme $Q_{10}$ to an organic layer, separating the organic layer containing reduced coenzyme $Q_{10}$ from an aqueous layer to give the organic layer, where necessary, washing the organic layer with water and substituting the solvent, and evaporating the solvent from the organic layer to give reduced coenzyme $Q_{10}$ as an oily substance or a solid.

The above-mentioned methods 1-3 are explained below.

In the above-mentioned method 1, reduced coenzyme $Q_{10}$ is precipitated (crystallized) from the reaction mixture successively after the reduction reaction. Needless to say, the purification and crystallization are particularly effectively performed when they also remove the impurities contained in the reaction mixture containing reduced coenzyme $Q_{10}$. In this way, coexistent impurities, particularly, an analogous compound having a similar structure (e.g., reduced coenzyme $Q_9$, reduced coenzyme $Q_8$, reduced coenzyme $Q_7$ etc.), which are generally not always easy to remove, can be removed.

In method 1, reduced coenzyme $Q_{10}$ can be crystallized by general crystallization operations such as cooling, concentration, solvent substitution, use of poor solvent and the like, which are used alone or in an appropriate combination. Particularly, cooling crystallization using a cooling operation alone or concurrently is preferable.

Reduced coenzyme $Q_{10}$ is preferably crystallized under a forced flow. To suppress formation of supersaturation, and perform smooth nucleation and crystal growth, or to achieve high quality, the mechanical power necessary for stirring per unit volume is generally preferably not less than about 0.01 kW/m$^3$, preferably not less than about 0.1 kW/m$^3$, more preferably not less than about 0.3 kW/m$^3$. The above-mentioned forced flow is generally produced by rotation of impeller. However, as long as the above-mentioned flow is obtained, an impeller does not always need to be used and, for example, a method by a liquid circulation and the like may be utilized.

For crystallization, a seed crystal is preferably added to suppress formation of supersaturation and perform nucleation and crystal growth smoothly.

Since the crystallization temperature (cooling temperature for crystallization) of reduced coenzyme $Q_{10}$ also varies depending on the kind of the crystallization solvent and crystallization method, it cannot be generally defined. For example, it is preferably not more than 25° C., more preferably not more than 20° C., especially not more than 15° C., among others not more than 10° C. The lower limit is the solidification temperature of the system. Generally, it is preferably performed at about 0-25° C.

To minimize the level of various impurities in the obtained reduced coenzyme $Q_{10}$, or to obtain a slurry with good properties, the amount of crystals produced per unit time during crystallization can be controlled. The preferable amount of crystal precipitation per unit time is, for example, not more than the rate of crystallization of about 50% of the total crystal precipitation (i.e., 50% of amount/hr at maximum) per unit time, preferably not more than the rate of crystallization of about 25% of the total crystal precipitation (i.e., 25% of amount/hr at maximum) per unit time. The cooling rate for cooling crystallization is generally not more than about 40° C./hr, preferably not more than about 20° C./hr.

The thus-obtained crystal of reduced coenzyme $Q_{10}$ can be obtained as a wet form by, for example, solid-liquid separation by centrifugation, pressurization filtration, reduced pressure filtration and the like, and further, cake washing as necessary. Moreover, a crystal of reduced coenzyme $Q_{10}$ can be obtained as a dry form by placing the wet form in a reduced pressure dryer (vacuum dryer) having an inside replaced with an inert gas, and drying the wet form under reduced pressure. It is preferable to obtain a dry form.

In method 1, to perform crystallization at a desired concentration or property etc., a solvent may be added as necessary. In this case, the solvent to be added is not particularly limited, and hydrocarbons, fatty acid esters, ethers, alcohols, fatty acids, ketones, nitrogen compounds (including nitriles, amides), sulfur compounds, water and the like can be mentioned. Among these, particularly, an organic solvent such as monovalent or divalent alcohol and/or ketones, preferably monovalent or divalent alcohol and/or water-soluble ketones, specifically, methanol, ethanol, 1-propanol, 2-propanol, acetone, methylethylketone and the like, more preferably ethanol, acetone and the like is preferably added. Crystallization is preferably performed in the presence of such organic solvent, since a reduced coenzyme $Q_{10}$ crystal superior in slurry property and crystallinity can be obtained.

On the other hand, from convenience of operation and the like, an organic solvent used as a reaction solvent during reduction reaction and/or water is preferably added. Thus, in method 1, it is particularly preferable to perform a reduction reaction in a water-containing organic solvent, which is a mixed solvent of an organic solvent such as methanol, ethanol, 1-propanol, 2-propanol, acetone, methylethylketone and the like, preferably ethanol, acetone and the like, and water, and continuously perform crystallization.

While the concentration of reduced coenzyme $Q_{10}$ in a solvent for crystallization is not particularly limited, an oxidation preventive effect of reduced coenzyme $Q_{10}$ in a solvent tends to further increase in a solution containing reduced coenzyme $Q_{10}$ at a high concentration. Therefore, crystallization at a concentration of generally not less than 1 part by weight, preferably not less than 2 parts by weight of the content of reduced coenzyme $Q_{10}$ per 100 parts by weight of a solvent is more effective.

In the above-mentioned method 2, an organic solvent and/or water are/is added to the reaction mixture after completion of the reduction reaction to separate into two layers of an organic layer containing reduced coenzyme $Q_{10}$ and an aqueous layer, thereby transferring reduced coenzyme $Q_{10}$ to the organic layer to give an organic layer containing reduced coenzyme $Q_{10}$ and, where necessary, the organic layer is washed with water or subjected to solvent substitution, reduced coenzyme $Q_{10}$ is crystallized from the organic layer and subjected to solid-liquid separation to give reduced coenzyme crystal.

In method 2, ascorbic acid and its analogue(s) used for reduction reaction and byproducts resulting from the reaction such as dehydroascorbic acid and its analogue(s) and the like are preferably transferred to an aqueous layer, and the obtained organic layer is more preferably washed with water to further remove the above-mentioned components remaining therein.

The organic solvent to be added to separate into two layers of the above-mentioned organic layer containing reduced coenzyme $Q_{10}$ and an aqueous layer is not particularly limited as long as it can separate an aqueous layer from an organic layer containing reduced coenzyme $Q_{10}$ when the organic solvent, or the organic solvent and water are added to the reaction mixture after completion of the reduction reaction. The organic solvent to be added here may be the same as or different from the organic solvent in the water-containing organic solvent used for the reduction reaction as a reaction solvent.

Examples of such organic solvent include hydrocarbons, fatty acid esters, ethers, alcohols, ketones, nitrogen compounds (including nitriles, amides), sulfur compounds and the like. In addition, when the aqueous layer and an organic layer containing reduced coenzyme $Q_{10}$ are separated by further adding water to the reaction mixture (water-containing organic solvent solution) after the reduction reaction, an organic solvent does not always need to be used. Needless to say, both an organic solvent and water may be added. To prevent reduced coenzyme $Q_{10}$ from being oxidized with molecule oxygen during transfer of reduced coenzyme $Q_{10}$ into an organic layer, or during washing of the organic layer with water, the organic solvent to be added is preferably at least one kind of hydrocarbons, fatty acid esters, ethers, nitriles, most preferably hydrocarbons.

Examples of the hydrocarbons include aliphatic hydrocarbon, aromatic hydrocarbon, halogenated hydrocarbon and the like. Particularly, aliphatic hydrocarbon and aromatic hydrocarbon are preferable, and aliphatic hydrocarbon is especially preferable.

While aliphatic hydrocarbon may be cyclic or acyclic, saturated or unsaturated and is not particularly limited, aliphatic hydrocarbon having 3 to 20 carbon atoms, preferably 5 to 12 carbon atoms, can be generally used.

Specific examples include propane, butane, isobutane, pentane, 2-methylbutane, cyclopentane, 2-pentene, hexane, 2-methylpentane, 2,2-dimethylbutane, 2,3-dimethylbutane, methylcyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane and the like.

Among these, saturated aliphatic hydrocarbon having 5 to 8 carbon atoms is preferable, and pentane, 2-methylbutane, cyclopentane, hexane, 2-methylpentane, 2,2-dimethylbutane, 2,3-dimethylbutane, methylcyclopentane, cyclohexane, heptane, 2-methylhexane, 3-methylhexane, 2,3-dimethylpentane, 2,4-dimethylpentane, methylcyclohexane, octane, 2,2,3-trimethylpentane, isooctane, ethylcyclohexane and a mixture thereof are particularly preferable used.

While the above-mentioned aromatic hydrocarbon is not particularly limited, normally, aromatic hydrocarbon having 6 to 20 carbon atoms, particularly 6 to 12 carbon atoms, especially 7 to 10 carbon atoms, is preferably used. Specific examples include benzene, toluene, xylene, o-xylene, m-xylene, p-xylene ethylbenzene, cumene, mesitylene, tetralin, butylbenzene, p-cymene, cyclohexylbenzene, diethylbenzene, pentylbenzene, dipentylbenzene, dodecylbenzene, styrene and the like. It is preferably toluene, xylene, o-xylene, m-xylene, p-xylene, ethylbenzene, cumene, mesitylene, tetralin, butylbenzene, p-cymene, cyclohexylbenzene, diethylbenzene or pentylbenzene, more preferably, toluene, xylene, o-xylene, m-xylene, p-xylene, cumene or tetralin, and most preferably cumene.

The above-mentioned halogenated hydrocarbon may be cyclic or acyclic, saturated or unsaturated, and is not particularly limited. In general, acyclic one is preferably used. Normally, chlorinated hydrocarbon and fluorinated hydrocarbon are preferable, and chlorinated hydrocarbon is particularly preferable. A halogenated hydrocarbon having 1 to 6 carbon atoms, particularly 1 to 4 carbon atoms, especially 1 or 2 carbon atoms, is preferably used.

Specific examples include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane and the like.

It is preferably dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene or 1,1,1,2-tetrafluoroethane, more preferably dichloromethane, chloroform, 1,2-dichloroethylene, trichloroethylene, chlorobenzene or 1,1,1,2-tetrafluoroethane.

Examples of the above-mentioned fatty acid esters include propionate, acetate, formate and the like. Particularly, acetate and formate are preferable, and acetate is especially preferable. While ester group is not particularly limited, in general, alkyl ester or aralkyl ester having 1 to 8 carbon atoms, preferably alkyl ester having 1 to 6 carbon atoms, more preferably alkyl ester having 1 to 4 carbon atoms, is preferably used.

Examples of propionate include methyl propionate, ethyl propionate, butyl propionate and isopentyl propionate.

Examples of acetate include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate and the like. It is preferably methyl acetate, ethyl acetate, propyl acetate, isopropyl acetate, butyl acetate, isobutyl acetate, sec-butyl acetate, pentyl acetate, isopentyl acetate, sec-hexyl acetate or cyclohexyl acetate, more preferably methyl acetate, ethyl acetate, propyl acetate, isopropyl acetate, butyl acetate or isobutyl acetate, and most preferably ethyl acetate.

Examples of formate include methyl formate, ethyl formate, propyl formate, isopropyl formate, butyl formate, isobutyl formate, sec-butyl formate, pentyl formate and the like. It is preferably methyl formate, ethyl formate, propyl formate, butyl formate, isobutyl formate or pentyl formate, and most preferably ethyl formate.

Ethers may be cyclic or acyclic, saturated or unsaturated, and are not particularly limited. Generally, saturated ones are preferably used. Normally, ether having 3 to 20 carbon atoms, particularly 4 to 12 carbon atoms, especially 4 to 8 carbon atoms, is preferably used.

Specific examples include diethyl ether, methyl tert-butyl ether, dipropyl ether, diisopropyl ether, dibutyl ether, dihexyl ether, ethylvinyl ether, butylvinyl ether, anisole, phenetole, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol dibutyl ether and the like.

Preferred are diethyl ether, methyl tert-butyl ether, dipropyl ether, diisopropyl ether, dibutyl ether, dihexyl ether, anisole, phenetole, butylphenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether and ethylene glycol monoethyl ether, more preferred are diethyl ether, methyl tert-butyl ether, anisole, dioxane, tetrahydrofuran, ethylene glycol monomethyl ether, ethylene glycol monoethyl ether, more preferably, diethyl ether, methyl tert-butyl ether, anisole, tetrahydrofuran and the like, and most preferably, methyl tert-butyl ether and tetrahydrofuran.

Nitriles may be cyclic or acyclic, saturated or unsaturated, and is not particularly limited. In general, saturated one is preferably used. Normally, nitrile having 2 to 20 carbon atoms, particularly 3 to 12 carbon atoms, especially 3 to 8 carbon atoms, is preferably used. Specific examples include acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphtonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenylcyclohexanecarbonitrile, tolylcyclohexanecarbonitrile and the like.

It is preferably propionitrile, succinonitrile, butyronitrile, isobutyronitrile, valeronitrile, methyl cyanoacetate, ethyl cyanoacetate, benzonitrile, tolunitrile or chloropropionitrile, more preferably acetonitrile, propionitrile, butyronitrile or isobutyronitrile.

Alcohols may be cyclic or acyclic, saturated or unsaturated and are not particularly limited. Generally, saturated ones are preferably used. Normally, monovalent alcohol having 1 to 20 carbon atoms, particularly 4 to 12 carbon atoms, especially 4 to 6 carbon atoms, is preferable.

Examples of the monovalent alcohol include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol and the like.

Preferred are 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol and cyclohexanol, more preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol and neopentyl alcohol, and further preferred are 1-butanol, 2-butanol, isobutyl alcohol, 2-methyl-1-butanol and isopentyl alcohol.

Examples of the divalent alcohol include 1,2-ethanediol, 1,2-propanediol, 1,3-propanediol, 1,2-butanediol, 1,3-butanediol, 1,4-butanediol, 2,3-butanediol, 1,5-pentanediol and the like.

Examples of the trivalent alcohol include glycerol and the like.

The ketones are not particularly limited, and normally, one having a carbon number of 3-6 is preferably used. Specific examples include acetone, methylethylketone, methylbutylketone, methylisobutylketone and the like, preferably methylethylketone.

Examples of the nitrogen compounds include nitromethane, formamide, N-methylformamide, N,N-dimethylformamide, N,N-dimethylacetamide, N-methylpyrrolidone and the like.

Examples of the sulfur compounds include dimethyl sulfoxide, sulfolane and the like.

As the water to be added in method 2, aqueous solutions such as brine and the like may be used since ascorbic acid and its analogues, other byproducts and the like can be efficiently transferred into an aqueous layer, production of an emulsion by mixing an aqueous layer and an organic layer can be avoided, and the like. In addition, when the aqueous layer and the organic layer are separated by mere addition of a solvent having low compatibility with the above-mentioned water to the reaction mixture after completion of the reduction reaction, water does not always need to be added.

In method 2, an organic layer containing reduced coenzyme $Q_{10}$, which is obtained by separation from an aqueous layer by adding an organic solvent and/or water to the reaction mixture, may be washed with water as necessary and directly crystallized. In this case, as an organic solvent to be used for reduction reaction or an organic solvent to be added after the above-mentioned reaction, at least one kind of hydrocarbons, fatty acid esters, ethers and nitriles is preferably used to prevent reduced coenzyme $Q_{10}$ from being oxidized with molecular oxygen during crystallization.

Needless to say, it is possible to obtain an organic layer containing reduced coenzyme $Q_{10}$ by using, as an organic solvent to be added after the above-mentioned reaction, hydrocarbons, fatty acid esters, ethers, alcohols, ketones, nitrogen compounds (including nitriles, amides), sulfur compounds and the like, substitute the solvent with other solvent, and then perform crystallization. Particularly, when a mixed solvent of monovalent or divalent alcohol or ketone, preferably monovalent or divalent alcohol or water-soluble ketone (specifically, methanol, ethanol, 1-propanol, 2-propanol, acetone, methylethylketone etc., preferably ethanol, acetone etc.) and water is used to perform crystallization, a reduced coenzyme $Q_{10}$ crystal having superior slurry property and crystallinity can be obtained. It is also a preferable embodiment to add a solvent such as hydrocarbons, fatty acid esters, ethers, alcohols, fatty acids, ketones, nitrogen compounds (including nitriles, amides), sulfur compounds, water and the like from the above aspect, preferably at least one kind of solvent from hydrocarbons, fatty acid esters, ethers and nitriles and water from the aspects of prevention of oxidation of reduced coenzyme $Q_{10}$ and removal of ascorbic acid and its analogues used as reducing agents, to give an organic layer containing reduced coenzyme $Q_{10}$, wash the layer with water as necessary, and substitute the solvent with monovalent or divalent alcohol or ketone to allow crystallization.

The method of the above-mentioned solvent substitution is not particularly limited. However, to shorten the solvent substitution operation, and suppress oxidation of reduced coenzyme $Q_{10}$ into oxidized coenzyme $Q_{10}$, the solvent is preferably evaporated at a melting temperature of reduced coenzyme $Q_{10}$ or above, and thereafter, desired other solvent is preferably added.

In method 2, crystallization from the above-mentioned organic layer and the treatments thereafter can be performed by methods similar to those in the above-mentioned method 1.

Also in the above-mentioned method 3, as in the above-mentioned method 2, ascorbic acid and its analogues used for reduction reaction and byproducts resulting from reaction such as dehydroascorbic acid and its analogues and the like are preferably transferred to an aqueous layer, and the obtained organic layer is more preferably washed with water to further remove the above-mentioned components remaining therein. Moreover, the kind of organic solvent and/or water to be added, the method of addition thereof, and the methods of transfer of reduced coenzyme $Q_{10}$ into the organic layer, washing of the obtained organic layer with water, solvent substitution and the like may be similar to those in the above-mentioned method 2.

In method 3, the method of evaporating the solvent from an organic layer containing reduced coenzyme $Q_{10}$ is not particularly limited as long as reduced coenzyme $Q_{10}$ free of solvent can be obtained. Reduced coenzyme $Q_{10}$ may be obtained as an oily substance or a solid. However, to shorten the operation and suppress oxidization of reduced coenzyme $Q_{10}$ into oxidized coenzyme $Q_{10}$, and in view of discharge ability from a concentration vessel, and the like, the solvent is preferably evaporated at not less than the melting temperature of reduced coenzyme $Q_{10}$ or a concentrate containing reduced coenzyme $Q_{10}$ as a main component (when the melting temperature has a range, not less than the melting start temperature) and an oily substance of reduced coenzyme $Q_{10}$ is obtained. Needless to say, it is also a preferable embodiment to obtain reduced coenzyme $Q_{10}$ as an oily substance and cool the oily substance to give a solid.

Among the above-mentioned methods 1-3, in view of easy handling of the obtained reduced coenzyme $Q_{10}$ and the like, it is preferably obtained as crystals as in the above-mentioned method 1 or method 2, and the above-mentioned method 1 is particularly preferable in view of the convenience of operation and the like.

The production method of the present invention is effectively performed under deoxidation atmosphere to prevent reduced coenzyme $Q_{10}$ from being oxidized. The deoxidation atmosphere can be achieved by replacement by an inert gas, decompression, boiling or using them in combination. It is preferred that the replacement by an inert gas, that is, an inert gas atmosphere is at least used. Examples of the above-mentioned inert gas include nitrogen gas, helium gas, argon gas, hydrogen gas and carbon dioxide gas, and nitrogen gas is preferred.

The production method of the present invention can drastically shorten the reaction time of reducing oxidized coenzyme $Q_{10}$ into reduced coenzyme $Q_{10}$, and can obtain high quality reduced coenzyme $Q_{10}$ economically with good workability.

EXAMPLES

While the present invention is explained in more detail in the following by referring to Examples, the present invention is not limited to those Examples alone. In the Examples, pH was measured using a pH meter D51 (manufactured by HORIBA, Ltd.). Moreover, the purity of reduced coenzyme $Q_{10}$, the weight ratio of reduced coenzyme ($Q_{10}$/oxidized coenzyme $Q_{10}$), and the like in the Examples were measured by the following HPLC analysis. However they do not define the limit value of the purity in the present invention nor do they define the upper limit value thereof.

(HPLC Analysis Conditions)

column; SYMMETRY C18 (manufactured by Waters) 250 (length) 4.6 mm (inner diameter), mobile phase; $C_2H_5OH:CH_3OH=4:3(v:v)$, detection wavelength; 210 nm, flow rate; 1 ml/min, retention time of reduced coenzyme $Q_{10}$; 9.1 min, retention time of oxidized coenzyme $Q_{10}$; 13.3 min.

Examples 1-3, Comparative Example 1

To aqueous ethanol (165 g) obtained by mixing ethanol (manufactured by Konishi Co., Ltd., special grade reagent) and water at the ratio shown in Table 1 were added oxidized coenzyme $Q_{10}$ (10 g) and L-ascorbic acid (6 g), and the mixture was stirred at 78° C. to perform a reduction reaction. The pH of the solution at the time the reduction reaction was started and the reaction time necessary for a reduced coenzyme $Q_{10}$/oxidized coenzyme $Q_{10}$ weight ratio to reach 99.5/0.5 are shown in Table 1. For comparison, the results obtained by using ethanol without water under the same conditions are also shown.

TABLE 1

|  | ethanol/water weight ratio | pH | reaction time (hr) |
|---|---|---|---|
| Comparative Example 1 | 100/0 | 3.2 | 26 |

TABLE 1-continued

| | ethanol/water weight ratio | pH | reaction time (hr) |
|---|---|---|---|
| Example 1 | 99/1 | 3.5 | 18 |
| Example 2 | 93/7 | 3.6 | 10 |
| Example 3 | 85/15 | 3.7 | 18 |

Example 4, Comparative Example 2

As shown in Table 2, to water-containing 2-propanol (165 g) obtained by mixing 2-propanol (manufactured by NACALAI TESQUE, INC., special grade) and water at a weight ratio of 90/10 were added oxidized coenzyme $Q_{10}$ (10 g) and L-ascorbic acid (6 g), and the mixture was stirred at 78° C. to perform a reduction reaction. The pH of the solution at the time the reduction reaction was started and the reaction time necessary for the weight ratio of reduced coenzyme $Q_{10}$/oxidized coenzyme $Q_{10}$ to reach 99.5/0.5 are shown in Table 2. For comparison, the results obtained by using 2-propanol without water under the same conditions are also shown.

TABLE 2

| | 2-propanol/water weight ratio | pH | reaction time (hr) |
|---|---|---|---|
| Comparative Example 2 | 100/0 | 2.9 | 34 |
| Example 4 | 90/10 | 3.6 | 16 |

Example 5, Comparative Example 3

As shown in Table 3, to water-containing acetone (100 g) obtained by mixing acetone (manufactured by Sanraizu Chemical Co., Ltd.) and water at a weight ratio of 85/15 were added oxidized coenzyme $Q_{10}$ (10 g) and L-ascorbic acid (6 g), and the mixture was stirred at 55° C. to perform a reduction reaction. The pH of the solution at the time the reduction reaction was started and the reduced coenzyme $Q_{10}$/oxidized coenzyme $Q_{10}$ weight ratio after a lapse of 24 hr are shown in Table 3. For comparison, the results obtained by using acetone without water instead of water-containing acetone are also shown.

TABLE 3

| | acetone/water weight ratio | pH | R |
|---|---|---|---|
| Comparative Example 3 | 100/0 | 2.3 | 36.9/63.1 |
| Example 5 | 85/15 | 2.8 | 85.8/14.2 |

R: reduced coenzyme $Q_{10}$/oxidized coenzyme $Q_{10}$ weight ratio

Example 6

To water-containing ethanol (165 g, weight ratio of ethanol/water=94/6) were added oxidized coenzyme $Q_{10}$ (10 g) and L-ascorbic acid (6 g), and the mixture was stirred at 78° C. to perform a reduction reaction at pH 3.5. After 13 hr, the ethanol solution was cooled to 2° C. at cooling rate of 10° C./hr with stirring to give a white slurry. The obtained slurry was filtered under reduced pressure, and wet crystals were washed with cold water-containing ethanol (ethanol/water weight ratio=94/6) (temperature of cold solvent used for washing was 2° C.). Furthermore, the wet crystals were dried under reduced pressure (20-40° C., 1-30 mmHg) to give white dry crystals (9.8 g, yield 98 mol %). All the above-mentioned operations were performed under a nitrogen atmosphere. The reduced coenzyme $Q_{10}$/oxidized coenzyme $Q_{10}$ weight ratio of the obtained crystals was 99.5/0.5, and the purity of reduced coenzyme $Q_{10}$ was 99.4%.

Example 7

To water-containing ethanol (165 g, weight ratio of ethanol/water=90/10) were added oxidized coenzyme $Q_{10}$ (10 g) and L-ascorbic acid (6 g), and the mixture was stirred at 78° C. to perform a reduction reaction at pH 3.5. After 13 hr, the ethanol solution was cooled to 50° C., and hexane (100 g) and water (100 g) were further added. The mixture was stirred and left standing to allow separation into 2 layers. The aqueous layer was removed, and the obtained organic layer was cooled to 2° C. at a cooling rate of 10° C./hr with stirring to give a white slurry. The obtained slurry was filtered under reduced pressure, and wet crystals were washed with cold water-containing ethanol (ethanol/water weight ratio=94/6) (temperature of cold solvent used for washing was 2° C.). Furthermore, the wet crystals were dried under reduced pressure (20-40° C., 1-30 mmHg) to give white dry crystals (9.5 g, yield 95 mol %). All the above-mentioned operations were performed under a nitrogen atmosphere. The reduced coenzyme $Q_{10}$/oxidized coenzyme $Q_{10}$ weight ratio of the obtained crystals was 99.5/0.5, and the purity of reduced coenzyme $Q_{10}$ was 99.4%.

Example 8

To water-containing ethanol (165 g, weight ratio of ethanol/water=90/10) were added oxidized coenzyme $Q_{10}$ (10 g) and L-ascorbic acid (6 g), and the mixture was stirred at 78° C. to perform a reduction reaction at pH 3.5. After 13 hr, the ethanol solution was cooled to 50° C., and hexane (100 g) and water (100 g) were further added. The mixture was stirred and left standing to allow separation into 2 layers. The aqueous layer was removed, and the solvent was evaporated under reduced pressure at an inside temperature of 50° C. while stirring the obtained organic layer to give a colorless transparent oily substance (9.9 g, yield 99 mol %). All the operations except depressurizing operation were performed under a nitrogen atmosphere. The reduced coenzyme $Q_{10}$/oxidized coenzyme $Q_{10}$ weight ratio of the obtained oily substance was 99.5/0.5, and the purity of reduced coenzyme $Q_{10}$ was 99.2%.

Comparative Example 4

To ethanol (1 L, manufactured by Konishi Co., Ltd., special grade reagent) were added oxidized coenzyme $Q_{10}$ (10 g) and L-ascorbic acid (4 g), and the mixture was stirred at 50° C. to dissolve oxidized coenzyme $Q_{10}$ and L-ascorbic acid. After dissolution, 0.05 M aqueous sodium hydroxide solution (100 mL) and water (150 mL) were added, and the mixture was stirred at the same temperature to perform a reduction reaction. The pH of the reaction mixture at this point was 6.3. The reduced coenzyme $Q_{10}$/oxidized coenzyme $Q_{10}$ weight ratio of the reaction mixture reached 95.8/4.2 in 5 hr from the start of the reaction, which was almost the same as the reduced coenzyme $Q_{10}$/oxidized coenzyme $Q_{10}$ weight ratio 3 hr later of 95.9/4.1. The mixture was heated to 78° C., and further reacted for 3 hr. However, the reduced coenzyme $Q_{10}$/oxidized coenzyme $Q_{10}$ weight ratio of the reaction mixture remained almost the same and was 96.1/3.9.

The invention claimed is:

1. A method of producing reduced coenzyme $Q_{10}$ comprising reducing oxidized coenzyme $Q_{10}$ with ascorbic acid and/or its analogue(s) using a water-containing organic solvent as a reaction solvent and performing the reduction reaction at pH 5 or below, wherein the weight ratio of the organic solvent and water in the water-containing organic solvent is within the range of 99/1-85/15.

2. The production method of claim 1, wherein the water-containing organic solvent is a mixed solvent of (a) at least one kind of water-soluble organic solvent selected from the group consisting of alcohols, ketones, nitriles and ethers, and (b) water.

3. The production method of claim 2, wherein the alcohol is at least one kind selected from the group consisting of methanol, ethanol, 1-propanol and 2-propanol.

4. The production method of claim 2, wherein the ketone is acetone.

5. The production method of claim 1, wherein the ascorbic acid and/or its analogue(s) are/is at least one kind selected from the group consisting of ascorbic acid, rhamno-ascorbic acid, arabo-ascorbic acid, gluco-ascorbic acid, fuco-ascorbic acid, glucohepto-ascorbic acid, xylo-ascorbic acid, galacto-ascorbic acid, gulo-ascorbic acid, allo-ascorbic acid, erythro-ascorbic acid, 6-desoxyascorbic acid, esters thereof and salts thereof.

6. The production method of claim 1, wherein the amount of the ascorbic acid and its analogues to be used for the reduction reaction is an effective amount that can convert oxidized coenzyme $Q_{10}$ to reduced coenzyme $Q_{10}$.

7. The production method of claim 6, wherein the ascorbic acid and its analogues are used in not less than one or more moles per mole relative to oxidized coenzyme $Q_{10}$ to be used.

8. The production method of claim 1, further comprising crystallizing reduced coenzyme $Q_{10}$ from a reaction mixture after the reduction reaction, and performing a solid-liquid separation to give a reduced coenzyme $Q_{10}$ crystal.

9. The production method of claim 1, further comprising adding, after the reduction reaction, an organic solvent and/or water to the reaction mixture to allow separation into an organic layer comprising reduced coenzyme $Q_{10}$ and an aqueous layer to give the organic layer, crystallizing the reduced coenzyme $Q_{10}$ from the organic layer, and performing a solid-liquid separation to give a reduced coenzyme $Q_{10}$ crystal.

10. The production method of claim 1, further comprising adding, after the reduction reaction, an organic solvent and/or water to the reaction mixture to allow separation into an organic layer comprising reduced coenzyme $Q_{10}$ and an aqueous layer to give the organic layer, and evaporating the solvent from the organic layer to give reduced coenzyme $Q_{10}$ as an oily substance or a solid.

11. The production method of claim 1, wherein the weight ratio of the organic solvent and water in the water-containing organic solvent is within the range of 95/5-90/10.

12. The production method of claim 1, wherein the reduction reaction is performed at pH 2 to 4.

13. The production method of claim 1, wherein the reduction reaction is completed in 20 hours.

* * * * *